(12) United States Patent
Milavetz

(10) Patent No.: US 6,420,107 B1
(45) Date of Patent: Jul. 16, 2002

(54) ASSAY FOR IDENTIFYING ANTI-VIRAL AGENTS SPECIFIC FOR PROTEIN-COATED DOUBLE-STRANDED DNA VIRUSES

(75) Inventor: Barry I. Milavetz, Grand Forks, ND (US)

(73) Assignee: University of North Dakota, Grand Forks, ND (US)

( * ) Notice: Subject to any disclaimer, the term of this patent is extended or adjusted under 35 U.S.C. 154(b) by 0 days.

(21) Appl. No.: 09/911,983

(22) Filed: Jul. 24, 2001

(51) Int. Cl.$^7$ ........................ C12Q 1/70; G01N 33/53
(52) U.S. Cl. ........................................ 435/5; 435/7.2
(58) Field of Search ........................................ 435/5, 7.2

(56) References Cited

PUBLICATIONS

Abstract entitled "Uncoating of SV40 Virions and Generation of a Nucleosome–Free Region" from presentation at International DNA Tumor Virus meeting of Jul. 1998, by Barry Milavetz, RaeJean Hermansen, and Michael Friez of Univ. of North Dakota.

*Primary Examiner*—Hankyel T. Park
(74) *Attorney, Agent, or Firm*—Kinney & Lange, P.A.

(57) ABSTRACT

The present invention is an assay for screening and identifying pharmaceutically effective compounds that specifically inhibit the uncoating of protein-coated double-stranded DNA viruses. Viral uncoating is monitored by fractionation and competitive polymerase chain reaction (PCR) techniques.

23 Claims, 8 Drawing Sheets

ASSAY FOR IDENTIFYING ANTI-VIRAL AGENTS SPECIFIC FOR PROTEIN-COATED DOUBLE-STRANDED DNA VIRUSES

CROSS-REFERENCE TO RELATED APPLICATION(S)

None.

BACKGROUND OF THE INVENTION

This invention relates to a method for screening potential anti-viral compounds. In particular, the present invention is an assay for testing a compound's ability to inhibit uncoating of protein-coated double-stranded DNA (dsDNA) viruses.

Viral infections have proven to be especially challenging for the medical field. So far, research has failed to find a cure for a viral infection, and many times the best that can be done is to relieve the symptoms associated with the illness. Even vaccines against viruses are not totally effective at blocking an infection. Therefore, attention has focused on stopping a viral infection during its initial stages of infection. This stops further spread and prevents the infection from developing into a productive disease state.

Protein-coated dsDNA viruses make up a class of viruses which have a wide spectrum of effects. Some are harmless while others cause life-threatening conditions. Families of viruses that are included are Papovavirus, Polyomavirus, Adenovirus, and Herpesvirus. Human Papilloma Virus (HPV) is a serious human pathogen that is thought to be the causative agent of a vast majority of diagnosed cervical cancers, and it falls into this category of viruses. Another example is Herpesvirus, which, though not usually life-threatening, can be very devastating.

The infection process of these similarly structured protein-coated dsDNA viruses is believed to be the same within all viral families that fall into this group. The process has been divided into three stages: adsorption to the surface of the cell, penetration of the cell membrane and transport to the nucleus, and uncoating (removal of capsid proteins) within the nucleus. Using a combination of biochemical fractionation and electron microscopy. the first two stages have been relatively well characterized. For example, these types of methods were used to study the Simian Virus 40 (SV40) and polyoma viruses. Both viruses followed a similar pattern where the majority of infecting virus was found on the cell surface fifteen minutes postinfection and maximal transport to the nucleus occurred at three hours postinfection.

BRIEF SUMMARY OF THE INVENTION

Viral uncoating has not been as well studied. Previous notions were that all virus that entered a cell was opened up, or uncoated, simply as a consequence of being inside the cell. The idea has recently emerged, however, that the process of uncoating is regulated and active and, thus, theoretically can be inhibited. Developing a system for screening and identifying compounds that inhibit this process would, therefore, be very advantageous in progressing available viral drug therapies.

The invention is an assay for identifying compounds that have anti-viral activity. Susceptible host cells are exposed to a potential viral inhibitor and then infected with a virus. The host cells are incubated to allow the virus to be transported to the nucleus and uncoated. The percentages of input virus appearing as intact virus and uncoated viral chromatin is determined. An effective inhibitor shows a decrease in uncoated viral chromatin with a corresponding increase in intact virus.

BRIEF DESCRIPTION OF THE DRAWINGS

FIG. 2a shows the amplification products generated from chromatin in gradient fractions using standard PCR.

FIG. 2b shows the amplification products generated from chromatin in gradient fractions using competitive multiplex PCR.

FIG. 5a shows the amplification products obtained from gradient fractions isolated from cells infected for 15 minutes and incubated for 6 hours.

FIG. 5b shows the amplification products obtained from gradient fractions isolated from cells infected for 15 minutes and challenged with a second virus at 3 hours postinfection.

DETAILED DESCRIPTION

It has long been believed that once a protein-coated dsDNA virus enters a host cell it uncoats through some spontaneous process. New evidence has emerged that suggests an active and regulated process controls viral uncoating. The present invention is designed to take advantage of this theory in order to screen and identify new anti-viral agents. The SV40 virus is a member of the Papovavirus family and serves as the model system for studying the theories that are the basis for this invention.

Amplifying the chromatin DNA is a necessary aspect of these studies and very useful for the invention described below. Polymerase Chain Reaction (PCR) is, to date, the best method of amplifying regions of DNA and is used to amplify the small quantities of SV40 chromatin present in the cells following the short infection times used in these studies. Initial analyses of chromatin are accomplished using standard PCR, while quantitation of chromatin is carried out using competitive multiplex PCR. In competitive multiplex PCR, a standard amount of a competitor DNA, which differs in size in the region to be amplified from the target DNA, is added to each reaction mixture prior to PCR. Since a constant amount of competitor DNA is used, its amplification product is used to normalize the product of the target DNA amplification reaction. The different size amplification products makes them easy to separate and detect.

Figure 1:
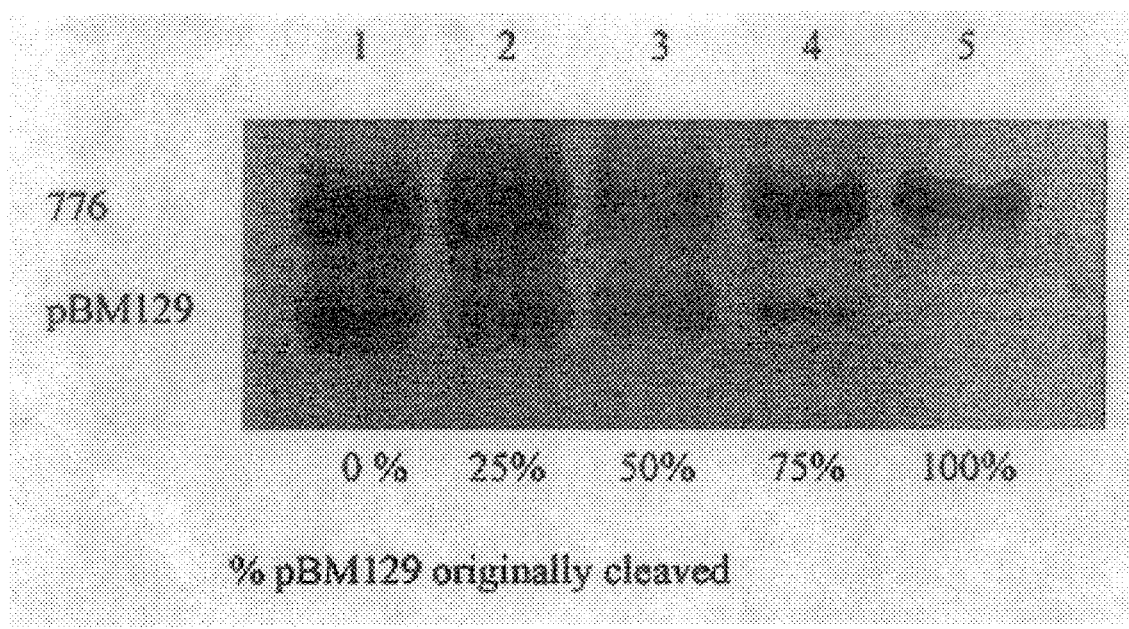
FIG. 1 is an example of multiplex PCR of SV40 DNA.

FIG. 1 shows results using PCR amplification of target and competitor DNA mixtures having various ratios of each DNA. This provides an indication of how well the PCR performs.

SV40 virus are grown in the following mainer. BSC-1 cell cultures are maintained in 75 cm² cell culture dishes containing Eagle's minimum essential medium supplemented with 10% fetal bovine serum and 100 µg/ml gentamicin at 37° C. Subconfluent monolayers of cells are infected with SV40 for one hour.

The nuclei are next prepared by first washing the cells with phosphate buffered saline and scraped into low ionic strength buffer containing 0.025% triton X-100 to break open the cells, and the nuclei are sedimented. The chromatin is extracted from the infected nuclei at low ionic strength. It is partially purified by sedimenting over a 10% glycerol step gradient on a cushion of 50% glycerol in a TLA 100.3 rotor at 50,000 rpm for 35 minutes in a Beckman TLA 100 ultracentrifuge. Any comparable sedimentation conditions would also be effective. 0.2 ml fractions are collected from the top of the gradient to the bottom. 25 µl to 100 µl aliquots, depending on the DNA concentration contained in the gradient fractions, are deproteinized using 10 µl of lysing solution (0.5% sodium dodecyl sulfate and 0.002 M ethylenediaminotetraacetate (EDTA)), and the final volume is adjusted to 200 µl with TE (10 mM tris and 2 mM EDTA, pH 7.4). The chromatin solution is extracted with phenol-chloroform and ethanol precipitated using standard methods. Preferably, ethanol precipitation is done in the presence of Pellet Paint according to the manufacturer's instructions. The precipitated DNA is then resuspended in 20 µl of TE.

The two forms of DNA shown here and in some of the subsequent figures are derived from the pBM129 and 776 strains of SV40. Amplification of the 776 DNA results in a product that is 72 base-pairs (bp) longer, because it contains two copies of an enhancer in the region which is amplified, whereas the pBM 129 DNA contains only one copy of the enhancer.

The PCR is carried out in a standard thermal cycler, such as a Perkin-Elmer model 480, using as primers the SEQ ID NO: 15'-GCAAAGCTTTTTGCAAAAGCCTAGGCCT-3' SEQ ID NO:2 5'CGAACCTTAACGGAGGCCTGGCG-3'. Hot start amplifications are conducted using 0.5 units of DNA polymerase, such as $Vent_R$, (exo-) DNA polymerase from New England Biolabs, using the manufacturer's reaction conditions. The DNA is amplified for 30 cycles with each cycle consisting of the following conditions: 95° C. for one minute, 66° C. for one minute, and 72° C. for one minute.

Following PCR amplification, the products are separated by submerged agarose gel electrophoresis on a 2.2% agarose gel. The DNA is stained with ethidium bromide and photographed under ultraviolet light, such as on a UVP GDS8000 gel documentation system. The resulting bands on the gels are quantitated by densitometry using a program such as the Biorad molecular analyst program version 1.4.

In FIG. 1, lanes 1–5 contain 0%, 25%, 50%, 75%, and 100% uncleaved pBM129 DNA, respectively, and a constant amount of uncleaved 776 DNA as competitor. The cleaved DNA will not amplify using PCR. The relative positions of the two products on the agarose gel are indicated. As can be seen, the amount of amplification of the target DNA, pBM 129, is directly proportional to the fraction of intact pBM129 DNA present. The greatest amount of target DNA product is present when only intact DNA is used (lane 1), and no product results if no intact target DNA is used (lane 5).

When the amplification products were quantitated by densitometry and normalized to the amounts of competitor DNA product, the values were within 10% of those expected. The close agreement between the observed and expected values indicates that the PCR assay is a reliable means of quantitating viral chromatin present in infected cells.

Figure 2C:
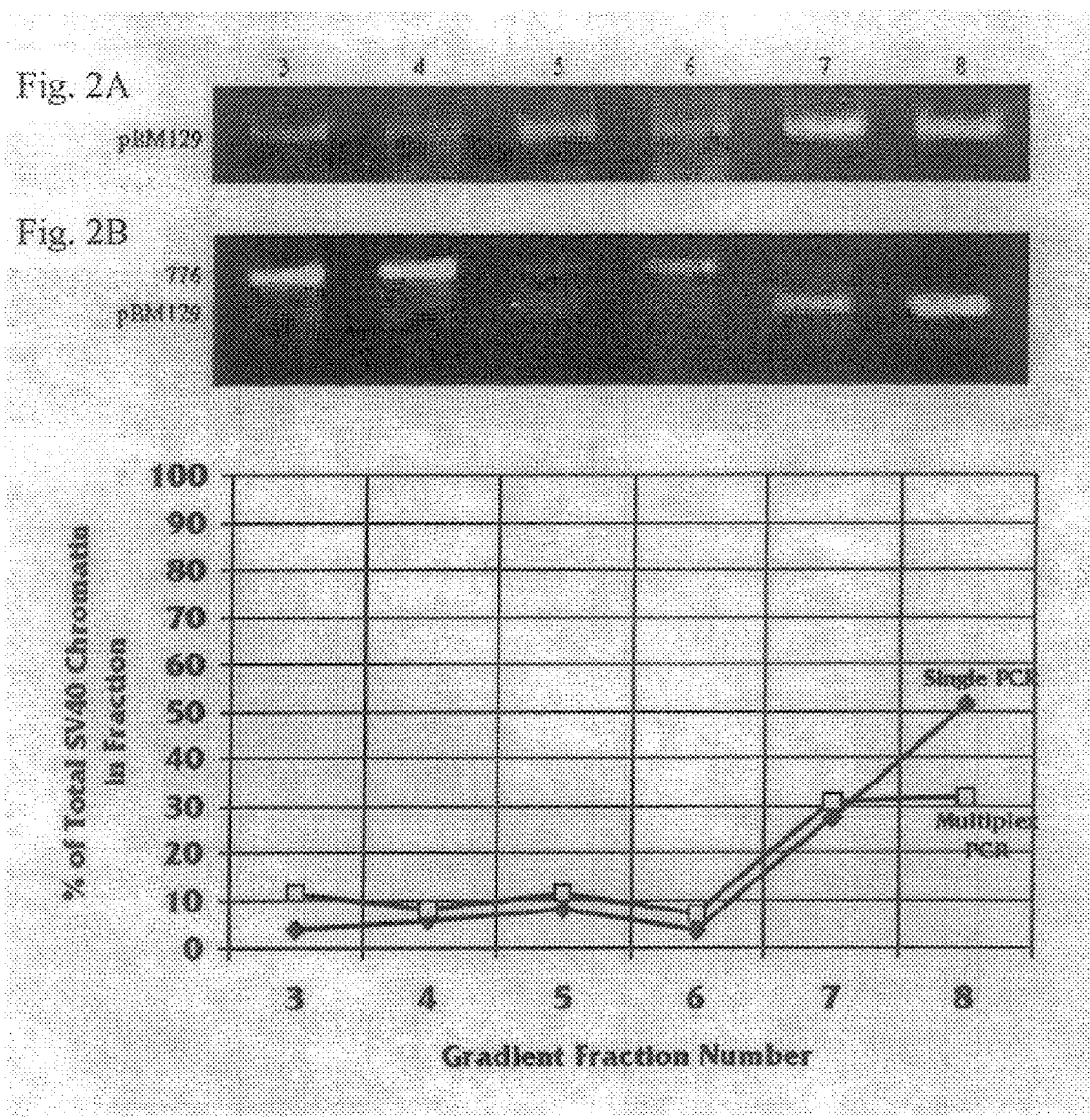
FIG. 2c is a graphic representation showing the percentage of total SV40 chromatin found in gradient fractions based on standard and multiplex PCR results.

FIGS. 2a, 2b, and 2c show typical results of standard and competitive multiplex PCR assays. FIG. 2a shows the amplification products generated from the chromatin in each gradient fraction. FIG. 2b shows the amplification products from each gradient fraction amplified in the presence of a constant amount of 776 DNA. The positions of the pBM129 and 776 products are indicated. FIG. 2c graphically shows the percentage of the total amount of SV40 chromatin found in each gradient fraction based on the amount of PCR product obtained by single and multiplex PCR. The horizontal axis represents the gradient fraction number, and the vertical axis represents the percentage of total SV40 chromatin in each fraction. Subsequent graphs use identical axes.

BSC-1 cells were infected for one hour with the pBM 129 virus and the viral chromatin was extracted, purified, and amplified as described above. The multiplex PCR included a constant amount of 776 competitor DNA. The actual amount of amplification is dependent on the relative amounts of DNA originally present in the amplification reaction. Where the competitor DNA is present in excess, it is the principle product, while the opposite is true when the target DNA is present in excess. Compare the amplification of fraction 3 with fraction 8 following multiplex PCR (FIG. 2b). Quantitation of the percentage of products produced by each gradient fraction is shown graphically in FIG. 2c. Although there are small differences in the amount of DNA amplified by each procedure from each gradient fraction, the overall pattern of the products is the same. The largest amount of amplified target DNA product was obtained from fractions 7 and 8, but target DNA product was obtained from all the fractions tested. Since SV40 chromosomes are expected to be found in fractions 3 to 5 and SV40 virions are expected to be in fractions 7 and 8 based upon prior experience with gradient separation of chromatin at later times in infection, these results are consistent with the uncoating of a fraction of input virus particles following the short infection time used.

Figure 3:
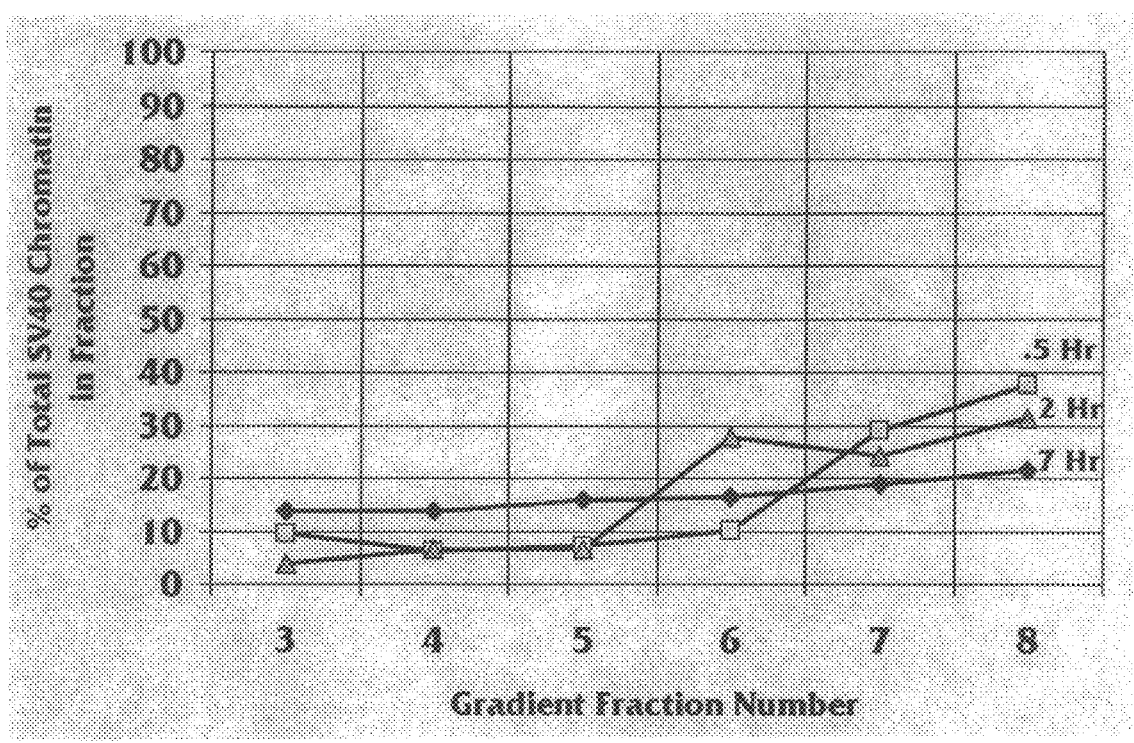
FIG. 3 is a graphic representation of the amount of SV40 uncoating following exposure of cells to virus for various periods of time.

Since the presence of both SV40 chromosomes and virus following a 1 hour infection could be the result of the relatively short time of the infection, the effect of the length of exposure to virus on the amount of uncoating was investigated. FIG. 3 graphically shows the patterns of SV40 chromatin obtained from infections done over various exposure times based upon PCR amplification.

BSC-1 cells were infected with pBM129 virus for 30 minutes, 2 hours, or 7 hours, and intracellular SV40 chromatin was isolated and purified as described above. The chromatin from each fraction was amplified, the PCR products separated by agarose gel electrophoresis, and then quantitated by densitometry. The percentage of the total amount of SV40 chromatin found in each gradient fraction based on the amount of PCR product obtained is shown. With the shortest infection time, the majority of the SV40 chromatin sedimented as virions (fraction 8), while after a 7 hour infection the pattern of sedimentation was much more evenly distributed. Even though a much larger proportion of input virus was present as SV40 chromosomes (fractions 4 and 5) after a 7 hour infection, a significant fraction (>20%) still sedimented as intact virions.

The presence of intact virus in fractions 7 and 8 following longer infection times may have been due either to an inhibition of uncoating or to the continual transport of fresh virus into the nucleus over the course of infection. To exclude the possibility that the internalized virus was a result of transport of fresh virus to the nucleus, a comparison was made between cells infected for short times and incubated in the absence of virus and cells continuously exposed to virus for identical times.

Figure 4:
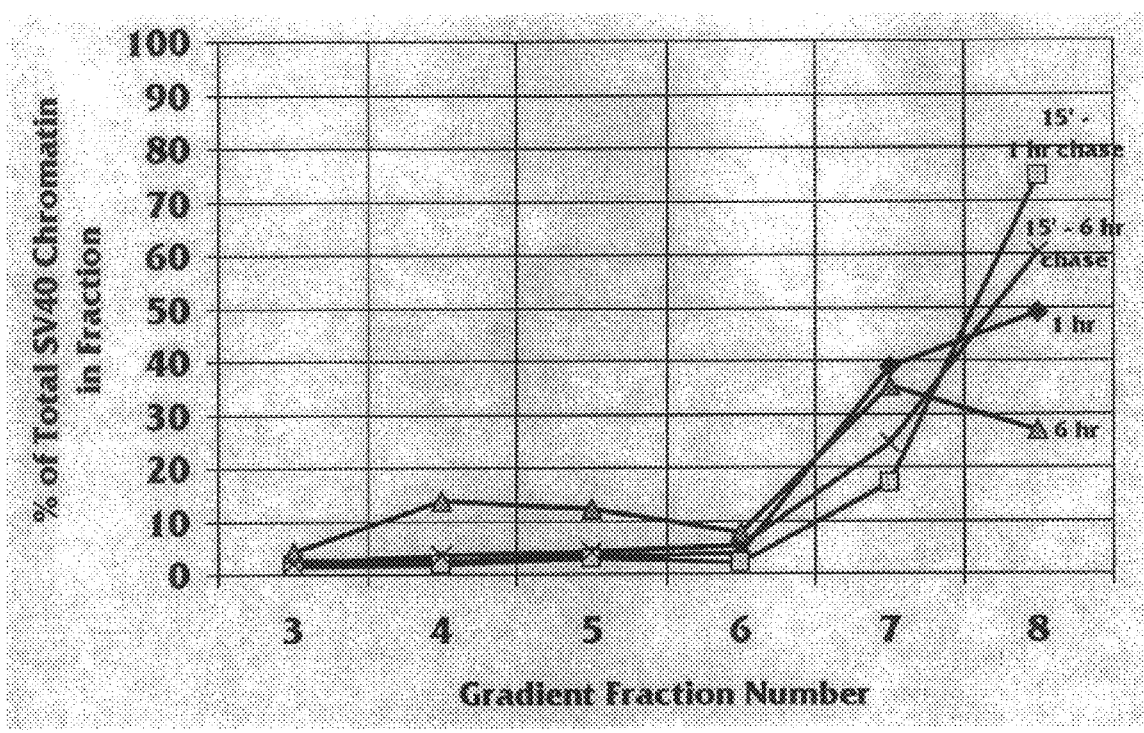
FIG. 4 is a graphic representation of the amount of SV40 uncoating following either continuous exposure to virus or following a short exposure to virus.

FIG. 4 shows the results of SV40 uncoatinig following short or continuous exposure infections. Cells were infected with pBM 129 virus for either 1 hour or 6 hours with continuous exposure to the virus or infected for 15 minutes, washed with fresh media, and incubated in fresh media for either a total of 1 hour or 6 hours. Intracellular SV40 chromatin was isolated, purified, and analyzed as in the previous figure.

Regardless of the infection conditions, both virus and chromosomes were observed in the nuclear extracts. However, differences in the proportion of each were observed. A 15 minute infection and 1 hour incubation resulted in most of the chromatin being contained within a viral particle with only a small portion being chromosomes. By comparison, continuous infections resulted in an increase in the proportion of uncoated chromosomes in a 1 hour infection and a further increase in a 6 hour infection. These results suggest that there is a rapid initial uncoating of virus following transport of the virus to the nucleus. Further uncoating appears to be inhibited since even after 6 hours of incubation a significant proportion of the chromatin still sediments as virus. However, the inhibition of uncoating observed in cells infected for short times appeared to be partially relieved by having virus present throughout the incubation period.

Figure 5C:
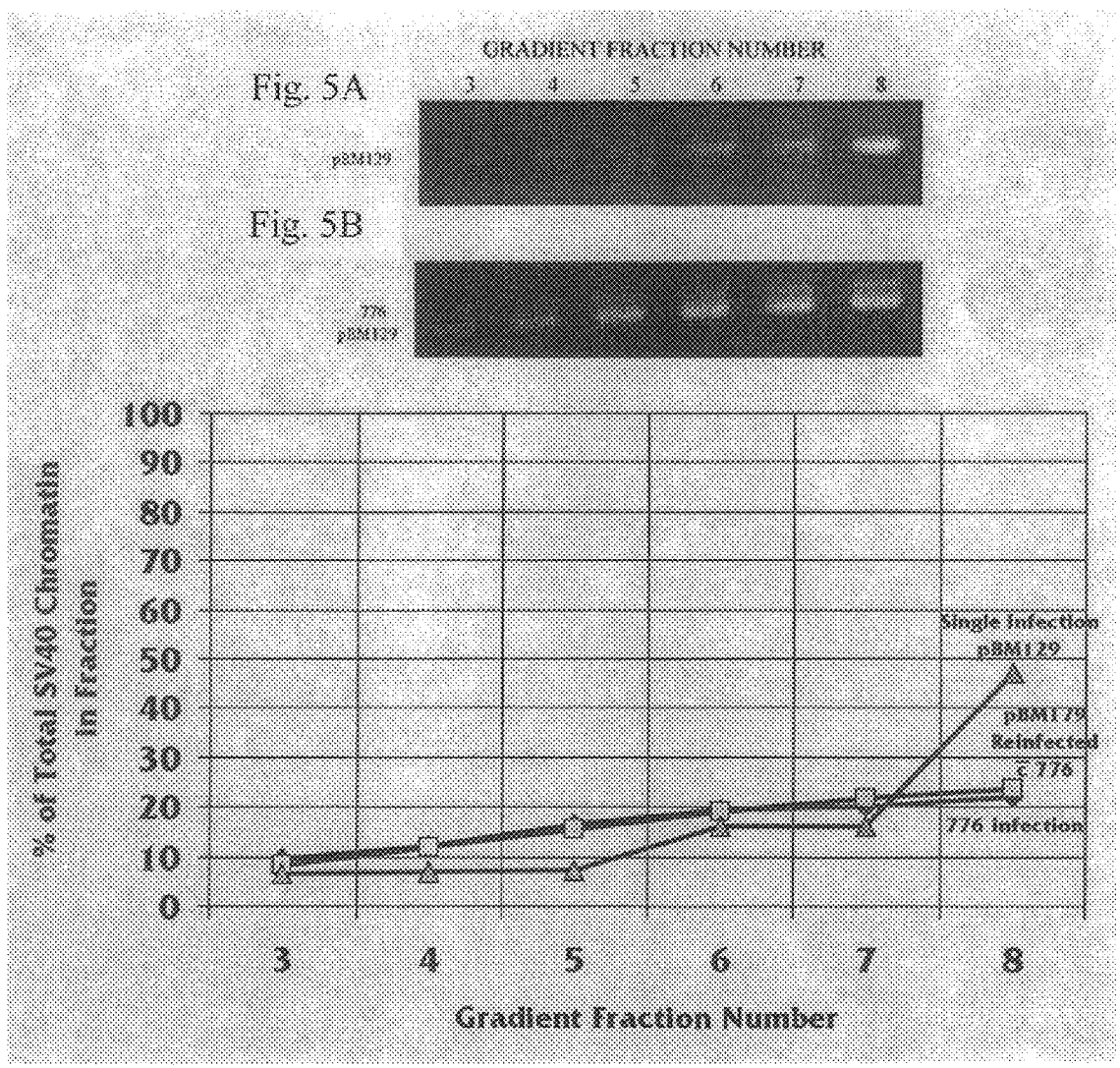
FIG. 5c is a graphic representation of the percentage of amplification products generated from gradient fractions shown in FIGS. 5a and 5b.

If the increase in uncoating seen in cells exposed to virus for longer times is a consequence of continuous exposure to virus, reinfecting cells originally infected for short times later in the incubation should duplicate this effect. FIGS. 5a, 5b, and 5c are the uncoating results of internalized SV40 virus following challenge with a second virus. Two plates of cells were infected with pBM129 virus for 15 minutes, washed to remove unbound virus, and incubated with fresh media. At 3 hours postinfection, one plate was challenged with 776 virus for 15 minutes, washed to remove unbound virus, and incubated for another 3 hours. As previously discussed, the 776 virus provides a PCR product which differs in size from the pBM129 PCR product. This allows preexisting cellular viruses to be distinguished from viruses used for reinfection. The second plate of cells was incubated without virus challenge. Intracellular chromatin was isolated, purified, and analyzed as previously described.

FIG. 5a shows the PCR products obtained from each gradient fraction isolated from cells which were unchallenged with a second virus. The position of the pBM129 PCR product is indicated. FIG. 5b shows PCR products obtained from each gradient fraction from cells challenged with a second virus. The positions of the pBM129 and 776 PCR products are indicated. FIG. 5c is a graphical representation of the percentage of PCR products generated from each gradient fraction shown in FIGS. 5a and 5b.

As expected, there was a significant increase in the fraction of SV40 chromatin present as chromosomes following the challenge with fresh virus compared to the sample that was not challenged with fresh virus. A significant amount of uncoating was also observed with virus used to challenge (FIGS. 5b and 5c). The effect of challenging with a second virus was similar regardless of the combination of viruses used or whether a second incubation of 3 hours was used following the 15 minute exposure to the challenging virus (data not shown). In the latter case, however, very little if any of the challenging virus was observed in the gradient fractions.

Figure 6:
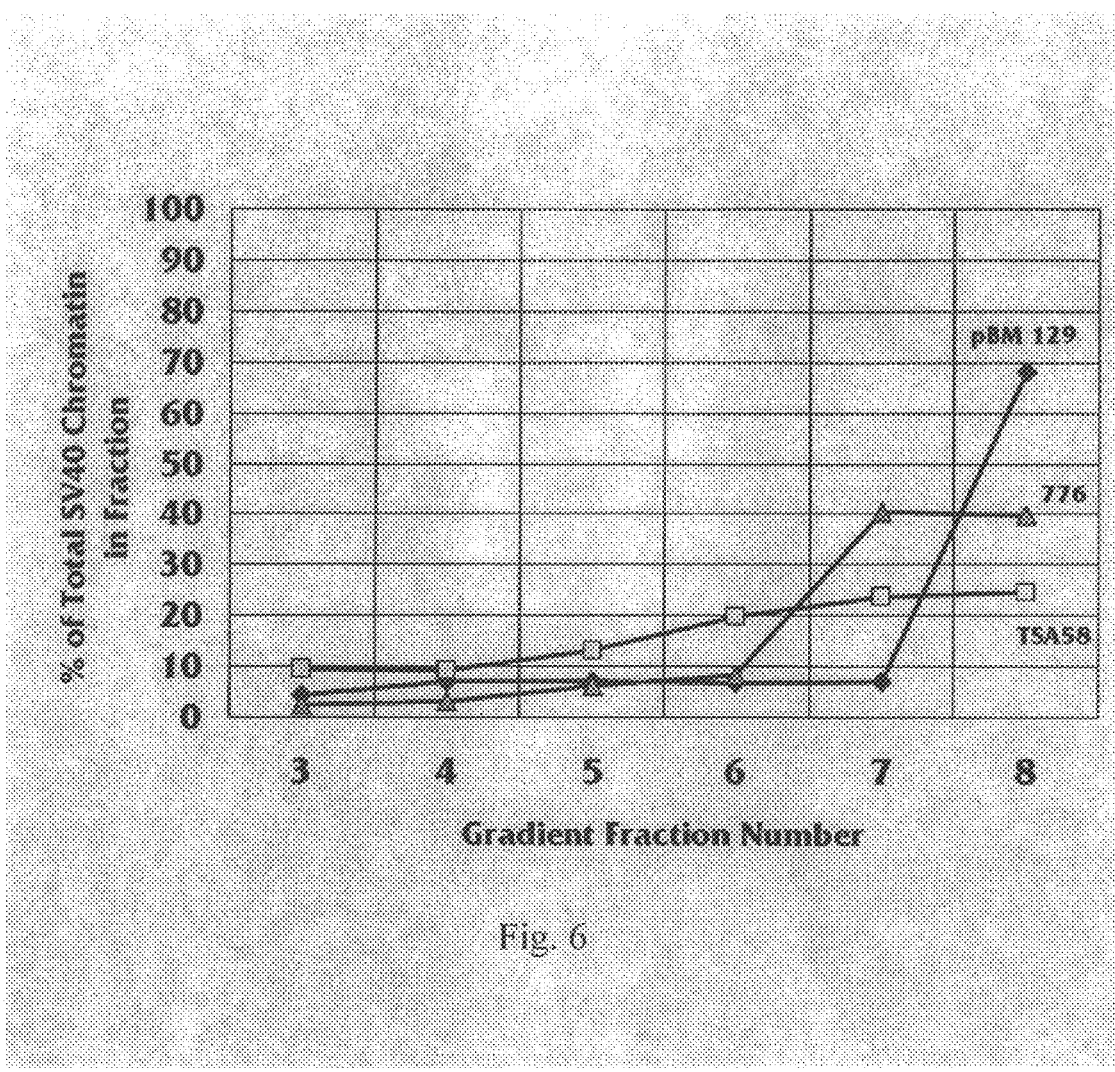
FIG. 6 is a graphic representation showing the percentage of amplification products generated from gradient fractions isolated from cells infected with either 776, pBM129, or tsA58 virus.

The observed inhibition in uncoating of the unchallenged viral infection could be a result of either the virus, the cell, or both inhibiting further uncoating. If the virus played a role in controlling uncoating, the most likely viral products responsible would be T-antigen, which is produced by early transcription or the late proteins, which are presumably removed from the virus. FIG. 6 graphically shows the results of experiments testing whether T-antigen plays a role in inhibiting viral uncoating.

The potential role of T-antigen in controlling uncoating was investigated by characterizing uncoating in the temperature-sensitive T-antigen mutant, tsA58. If functional T-antigen was required to inhibit uncoating, more uncoated virus should result with tsA58 than with a corresponding wild-type virus. For this experiment, cells were infected for 15 minutes at 37° C., which is in the temperature range at which tsA58 produces nonfunctional T-antigen, with either 776, pBM129, or tsA58 virus. The infected cells were washed free of unbound virus and incubated for a total of 6 hours. The chromatin was isolated, purified, and analyzed as before. The percentages of PCR products generated from each gradient fraction for each viral infection are indicated in FIG. 6.

As shown, both the pBM129 and 776 viral infections resulted in relatively small amounts of uncoated chromosomes with the bulk of the chromatin existing as virus in fractions 7 and 8. In contrast, the chromatin pattern from the tsA58 infection looked more like a long term infection (see FIGS. 3 and 4) with a much smaller intact virus peak and proportionately larger chromosome fraction. Similar results were observed with tsA58 infections at 34° C. and 40° C. (data not shown). The increased uncoating seen with the tsA58 mutant suggests that a fully functional T-antigen can inhibit the uncoating process and further suggests that uncoating is a regulated process.

Restriction endonuclease sensitivity has been extensively used as an assay to measure the percentage of SV40 chromosomes that are nucleosome-free at a particular restriction site. This assay is based on the observation that restriction endonucleases, which recognize palindromic sequences, require the sequence to bc protein-free in order to be digested. SV40 chromosomes have increased sensitivity at restriction sites within the promoter relative to other sites when analyzed this way. This increased sensitivity is most obvious at the Bgl I site.

Figure 7:
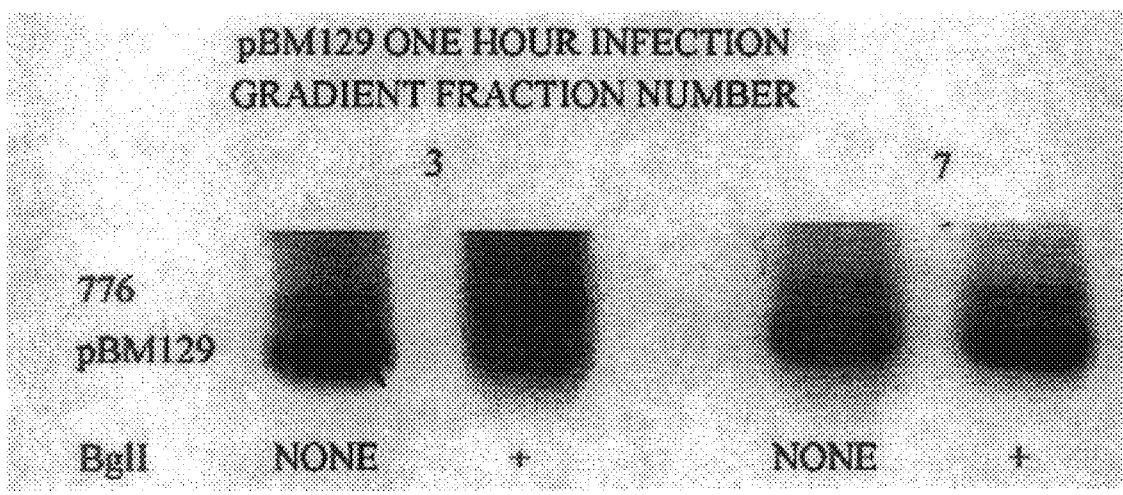
FIG. 7 shows the amplification products from SV40 chromatin cleaved by restriction endonuclease digestion using competitive multiplex PCR.

FIG. 7 shows typical examples of competitive multiplex PCR analysis of SV40 chromatin cleaved by Bgl I. Samples of pBM 129 chromatin from gradient fractions 3 and 7 obtained from 1 hour infections were incubated with or without Bgl I, and the DNA products were purified and amplified in the presence of a constant amount of 776 DNA. The amplification products were then separated by agarose gel electrophoresis and visualized. The positions of the expected amplification products from the pBM129 and 776 DNA are indicated.

pBM129 chromatin from fraction 3, which is expected to contain SV40 chromosomes, is efficiently cleaved at the Bgl I site, while chromatin from fraction 7, which is expected to contain intact or slightly opened virions, is not efficiently cleaved. Quantitative densitometry of the bands showed that approximately 80% of the chromatin in fraction 3 was cleaved, while only about 35% of the chromatin in fraction 7 was cleaved. The high sensitivity of the chromatin in fraction 3 to Bgl I digestion is consistent with its identification as SV40 chromosomes. Similarly, the low levels of digestion in fraction 7 are consistent with the expected presence of virions, which are resistant to restriction endonuclease digestion. The values of 80% and 35% are comparable to values previously reported for SV40 chromosomes and virions obtained at times much later in infection.

The nucleosome-free promoter region could appear more or less coordinately with the uncoating of virions if the processes are linked, or the nucleosome-free promoter region could appear more slowly if uncoating occurs significantly quicker than the generation of the nucleosome-free promoter. In the former case, SV40 chromosomes that are highly sensitive to Bgl I after relatively short uncoating times would be expected, while in the latter case, the SV40 chromosomes should have significantly lower sensitivities at the Bgl I site. With longer uncoating times, however, the sensitivity of the chromosomes should increase.

Figure 8:
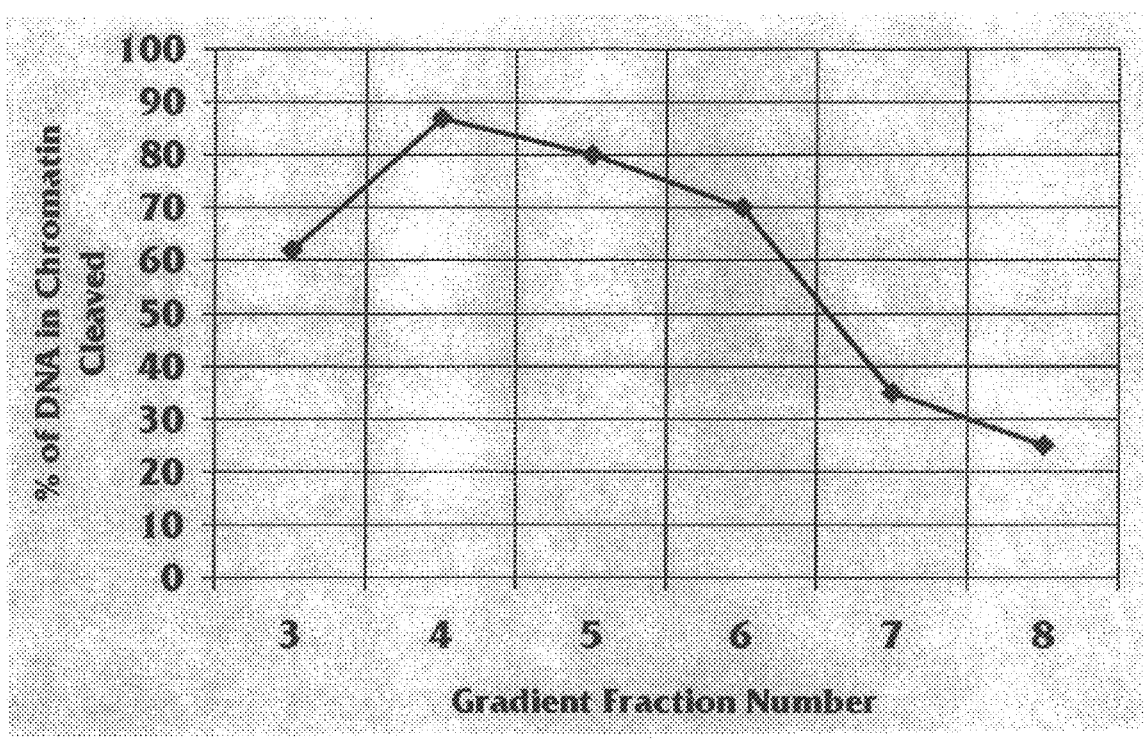
FIG. 8 is a graphic representation showing restriction endonuclease sensitivity of uncoating intermediates.

FIG. 8 graphically shows the results of determining the approximate kinetics of the appearance of the nucleosome-free promoter region. Cells were infected with pBM129 virus for 1 hour and the chromatin was isolated, purified, digested, and amplified as described in FIG. 7. The percent cleavage of each sample was determined by densitometry and normalized against the 776 control DNA. The percentage of the DNA originally present in the chromatin that was cleaved in each fraction is indicated.

The Bgl I sensitivity of fractions 3, 4, and 5, which consists primarily of SV40 chromosomes, was high. In contrast, the sensitivity of fractions 7 and 8, which contains mostly virions, was low. There was a clear increase in going from the bottom of the gradient to the top with an apparent plateau of sensitivity at the top. The maximal level of nuclease sensitivity observed at 1 hour in SV40 chromosomes, 80%, was essentially the same as was obtained for SV40 chromosomes incubated for much longer times either with or without continuous exposure to virus (data not shown). These results suggest that the nucleosome-free promoter region is generated either along with uncoating or shortly thereafter.

The rapid internalization of virus observed in this study is consistent with previously reported results, and the more or less coordinate uncoating of virions associated with the internalized virus has also been observed. However, there is a small difference with respect to timing of uncoating described in this study compared to previous studies. Previously, uncoating was thought to begin 2 to 3 hours postinfection. In the present analysis, uncoating was seen as early as 15 minutes postinfection. Identification of uncoated chromosomes at 15 minutes postinfection in this study is most likely due to the use of PCR to detect the low levels of SV40 chromatin present in cells following short infection times. PCR is a very sensitive analytical tool and is capable of amplifying very low amounts of input signal. In the previous studies, significantly less sensitive assay systems were utilized, and the relatively small amounts of uncoated chromatin present at the very early times could easily have been missed.

Cells continuously exposed to virus for 7 hours resulted in approximately 80% of the internalized virus being completely or partially uncoated chromosomes with the rest present as intact virions (FIG. 3). In contrast, cells exposed to virus for only 15 minutes and then incubated for 6 hours showed only a small fraction of uncoated internalized virus. The amount of uncoating present in cells continuously exposed to virus was similar to or somewhat less than the amount of uncoating described in previous studies where all or almost all of the internalized virus was uncoated. However, the amount of uncoating in cells exposed to virus for a short time was much less than expected. Since the fraction of internalized virus from a 15 minute infection could be significantly increased by challenging the infected cells with fresh virus, it seems likely that differences in the amount of uncoating in the various studies reflect differences in the exposure of cells to virus. Further, this result suggests that uncoating occurs by a mechanism in which the cell is stimulated to uncoat virus as a consequence of the exposure of the cell to the virus, presumably through a signal transduction-mediated process. All of the previous studies were characterized by infections using saturating amounts of virus or continuous exposure to virus. These conditions would be expected to lead to extensive uncoating based on an uncoating model where exposure to virus stimulates uncoating.

These studies also indicate that the formation of the nucleosome-free promoter region necessary for early transcription occurs either along with uncoating of the chromosomes or shortly thereafter. SV40 chromosomes containing a nucleosome-free promoter region were observed as early as 30 minutes postinfection. Although this is earlier than 4 hours postinfection, which was previously reported, the difference, again, probably reflects the difference in relative sensitivities of the assays used.

Based on these results, the structure of the SV40 virion, and the properties of the viral structural proteins, uncoating might be expected to occur in three stages. In the first stage, the interactions between adjacent pentons, which make up the capsid, would be expected to be disrupted. These interactions primarily consist of protein-protein binding between the carboxy terminus of vp-1, amino acids 315 to 344, on one penton and the core of a vp-1 in an adjacent penton and are stabilized by a $Ca^{++}$ binding site. Adjacent pentons may also be linked together by disulfide bonds. In the mature virion, cysteine 104 of vp-1 is located veryclose to asimilarcysteine in avp-1 moleculeofan adjacent penton. Disulfide linkages, however, are not thought to be the primary form of penton-penton bridge. Removal of $Ca^{++}$ and disruption of disulfide bonds in vitro have been shown to disrupt virions of SV40 and polyoma and may play a role in the uncoating of these viruses. Disruption of disulfide bonds has been suggested to be responsible for uncoating of the related papillomavirus, bovine papillomavirus.

Alternatively, disruption of penton-penton interactions could occur by proteolysis of the invading arm of the carboxy tenninus of vp-1. Proteolysis is involved in the uncoating of adenovirus and has been suggested to be responsible for uncoating of other viruses. Either proteolysis or changes in local $Ca^{++}$ concentrations could be regulated by the cell through signal transduction and could serve as mechanisms of uncoating consistent with the results obtained here. Although activation of signal transduction pathways have not previously been implicated in uncoating virus, activation of other cellular responses have been linked to viral binding to cell surfaces, such as activation of c-fos and c-myc and apoptosis following binding by bovine herpesvirus 1 glycoproteins. Regardless of how the penton-penton interactions are disrupted, the product of the first stage of uncoating would be expected to be chromosomes containing bound, unlinked pentons.

In the second stage of uncoating, the pentons which remain bound to the chromosomes following disruption of the penton-penton interactions would be expected to be removed. All of the SV40 and polyoma structural proteins are capable of binding to DNA through specific interactions between regions that contain basic amino acids present in the proteins and the DNA. Disruption of penton-chromosome interactions could occur either by masking the charge of the basic amino acids by acetylation, methylation, or phosphorylation or by proteolytic cleavage of the basic region of the proteins. Interestingly, both vp-2 and vp-3 of SV40 contain the sequence, asp-glu-ala-asp, and polyoma virus proteins contain the corresponding sequence, asp-asp-ala-asp. These are very similar to the caspase 3 target sequence, asp-glu-val-asp, found in the poly(ADP-ribose) polymerase. Activation of the caspase pathway and subsequent proteolysis of vp-2 and vp-3 would also be consistent with the stimulation of uncoating that was observed in this study.

In the third stage of uncoating, chromatin remodeling would be expected to generate a nucleosome-free promoter region. Since the chromatin in the virion consists of histones which are highly acetylated, chromatin remodeling may occur through a mechanism dependent upon the ability of acetylated histones to be displaced by competing binding factors.

The present invention is based on the finding that opening of the virus particle is regulated and dependent on activation of cellular pathways. The invention consists of a series of associated techniques that identify a new class of antiviral drugs, which function by inhibiting uncoating of an infecting protein-coated dsDNA virus. Since uncoating is a regulated and active process, as shown above, it is possible, through the use of an appropriate inhibitor, to block uncoating and prevent viral infection.

Appropriate cells are grown in culture by standard procedures and infected with virus for 15 to 30 minutes. This may vary according to the specific virus being tested. Examples of these input viruses include Polyomaviruses, Papovaviruses, Adenoviruses, Herpesviruses, or any protein-coated dsDNA viruses. Unbound virus is removed by washing the cells repeatedly with fresh sterile media, and the cells are incubated for an additional 6 hours, which allows the virus to uncoat. Again, the timing may vary with the type of virus. The fraction of uncoated virus is determined as described above.

The basal level of uncoating is determined by carrying out the assay in the absence of any putative inhibitor. A putative inhibitor is added to a second set of cells concurrently with the virus or very near the time of addition of the virus, and the level of uncoating is determined and compared to the basal level. If the level of uncoating in cells exposed to the putative inhibitor is less than the basal level, the inhibitor is a candidate for being a therapeutic agent. Accordingly, if the level of uncoating in the exposed cells is comparable to the basal level, the inhibitor is not a candidate for being a therapeutic agent.

Preferably, uncoating is stimulated to higher levels by the addition of more virus at later times in the incubation, or more preferably by the addition of an activator such as phorbol 12-myristate 13-acetate (TPA). TPA is a phorbol ester that is known to stimulate a number of signal transduction pathways, including the pathway that uncoats SV40. Stimulating uncoating in the assay makes the relative levels of uncoating higher and makes them easier to measure. Here, the putative inhibitor could be added with the initial input virus or just prior to the addition of the stimulating virus or activator compound. A potential therapeutic agent would be expected to block the increase in uncoating associated with the activation of the signal transduction pathway.

Once a potential therapeutic agent is identified, it could be used prophylactically to prevent infections when a person can reasonably expect to be exposed to a virus or following other treatments in order to limit the spread of a virus to uninfected neighboring cells.

This assay may also be scaled down to a micro-level in order to allow rapid analysis of many putative inhibitors. Assays can be automated and carried out in microtiter plates. A first round of elimination using a modified assay technique can also speed the process by narrowing down the number of agents being tested with the preferred assay. In the modified assay, virus is extracted from cells infected and treated with a putative agent. One fraction is treated with endonuclease, and a second fraction is left untreated. DNA present in unopened viral particles is resistant to digestion by the endonuclease, while DNA from uncoated viral particles is completely digested. A measurement of the amount of viral DNA in both fractions gives the approximate ratio of the fraction of input virus that has uncoated. The candidate agents that appear to inhibit uncoating in the modified assay would subsequently be analyzed using the preferred assay.

The signal transduction pathway that activates a particular virus may vary from virus to virus. Therefore, it may be necessary to determine appropriate activators for different viruses. Additionally, once an activator is identified using the assay, further experimentation could reveal the specific signal transduction pathway used by the cell to uncoat the virus. Other compounds could subsequently be designed that inhibit that pathway if the original inhibitor could not be used therapeutically for some reason. The designed compounds would most likely act on cellular factors that are acted upon by the original inhibitor.

Although the present invention has been described with reference to preferred embodiments, workers skilled in the art will recognize that changes may be made in form and detail without departing from the spirit and scope of the invention.

What is claimed is:

1. An assay for identifying compounds having anti-viral activity, comprising:

exposing susceptible host cells to a putative viral inhibitor;

infecting the host cells with input virus;

incubating infected host cells to allow viral uncoating; and determining an extent of uncoating which has occurred.

2. The assay of claim 1 wherein the input virus is a protein-coated double stranded DNA virus.

3. The assay of claim 1 wherein the input virus is a virus selected from the group consisting of Polyomavirus, Papovirus, Adenovirus, and Herpesvirus.

4. The assay of claim 1 and further comprising:

removing unbound input virus after infection.

5. The assay of claim 1 and further comprising:

lysing the infected host cells after are incubating to allow uncoating;

purifying nuclei;

isolating a mixture of intact virus and uncoated viral chromatin from the nuclei;

fractionating the mixture to isolate the intact virus and uncoated viral chromatin; and purifying viral DNA from the intact virus fraction and the uncoated viral chromatin fraction.

6. The assay of claim 1 wherein a percentage of input virus appearing as intact virus and uncoated chromatin is determined by a technique that amplifies viral DNA.

7. The assay of claim 6 wherein DNA amplification is carried out by polymerase chain reaction (PCR).

8. The assay of claim 1 wherein viral uncoating is increased by adding fresh virus during the infected host cell incubation.

9. The assay of claim 8 wherein the putative inhibitor is added just prior to addition of the fresh virus.

10. The assay of claim 1 wherein viral uncoating is increased by adding cellular signal transduction activator during the infected host cell incubation.

11. The assay of claim 10 wherein the cellular signal transduction activator is phorbol 12-myristate 13-acetate (TPA).

12. The assay of claim 10 wherein the putative inhibitor is added just prior to addition of the cellular transduction activator.

13. The assay of claim 1 wherein detennining an effective compound results when addition of the compound decreases the percentage of uncoated viral protein and increases the percentage of intact virus.

14. The assay of claim 13 and further comprising:

identifying a cellular transduction pathway inhibited by the compound; and designing a second compound that inhibits the cellular transduction pathway.

15. An assay for identifying a putative protein-coated double-stranded DNA viral inhibitor, comprising:

infecting susceptible host cells with an input virus;

removing unbound input virus;

incubating the host cells to allow viral uncoating;

adding a putative viral inhibitor to the host cells;

stimulating viral uncoating;

determining a percentage of input virus appearing as intact virus and uncoated viral chromatin.

16. The assay of claim 15 wherein viral uncoating is stimulated by adding fresh virus or a compound that activates an appropriate signal transduction pathway.

17. The assay of claim 15 wherein identifying the putative viral inhibitor as an effective viral inhibitor is indicated when a decrease in the percentage of uncoated viral chromatin and corresponding increase in intact virus results.

18. The assay of claim 17 and further comprising:

designing a second inhibitor that acts on cellular factors acted on by the effective viral inhibitor.

19. An assay for identifying compounds that inhibit viral uncoating, comprising:

infecting host cells grown in culture with an input virus;

removing unbound virus;

incubating the infected host cells to allow viral uncoating;

adding a test compound to the infected host cells;

stimulating viral uncoating by adding TPA;

purifying the nuclei by lysing the host cells and sedimenting the nuclei by centrifugation;

isolating a mixture of intact virus and uncoated viral chromatin by low-salt leaching;

fractionating the mixture into intact virus and uncoated viral chromatin by glycerol gradient sedimentation;

purifying DNA from each fraction;

amplifying the DNA from each fraction by competitive PCR; and determining percentages of input virus as intact virus and uncoated viral chromatin.

20. The assay of claim 19 wherein the input virus is a virus selected from the group consisting of Polyomavirus, Papovirus, Adenovirus, and Herpesvirus.

21. The assay of claim 19 wherein viral uncoating is stimulated by the addition of fresh virus.

22. The assay of claim 19 wherein the test compound is added to the host cells prior to infection by input virus and viral uncoating is not stimulated.

23. The assay of claim 17 and further comprising:
   identifying an effective compound based on the percentages of intact virus and uncoated viral proteins;
   identifying a cellular transduction pathway inhibited by the effective compound; and
   designing a compound that inhibits the cellular transduction pathway identified.

* * * * *

UNITED STATES PATENT AND TRADEMARK OFFICE
CERTIFICATE OF CORRECTION

PATENT NO. : 6,420,107 B1
DATED : July 16, 2002
INVENTOR(S) : Barry L. Milavetz

It is certified that error appears in the above-identified patent and that said Letters Patent is hereby corrected as shown below:

Column 3,
Line 5, delete "mainer", insert -- manner --
Line 40, after "the" insert -- obligonucleotides --
Line 41, delete "NO: 15'", insert -- NO: 1 5' --
Lines 41 and 42, after "3", insert -- and --

Column 5,
Line 8, delete "uncoatinig", insert -- uncoating --

Column 6,
Line 45, delete "bc", insert -- be --

Column 8,
Line 39, delete "veryclose", insert -- very close --
Line 50, delete " tenninus", insert -- terminus --

Column 10,
Line 40, delete "detennine", insert -- determine --

Column 11,
Line 64, delete "detennining", insert -- determining --

Signed and Sealed this

Fifteenth Day of April, 2003

JAMES E. ROGAN
*Director of the United States Patent and Trademark Office*

SEQUENCE LISTING

```
<160> NUMBER OF SEQ ID NOS: 2

<210> SEQ ID NO 1
<211> LENGTH: 28
<212> TYPE: DNA
<213> ORGANISM: Simian virus 40
```

-continued

```
<400> SEQUENCE: 1
gcaaagcttt ttgcaaaagc ctaggcct                                    28

<210> SEQ ID NO 2
<211> LENGTH: 23
<212> TYPE: DNA
<213> ORGANISM: Simian virus 40

<400> SEQUENCE: 2
cgaaccttaa cggaggcctg gcg                                         23
```